(12) United States Patent
Schewe et al.

(10) Patent No.: US 7,435,077 B2
(45) Date of Patent: Oct. 14, 2008

(54) CATHETER BALLOON MOLDING DEVICE

(75) Inventors: Scott Schewe, Eden Prairie, MN (US);
Jeffrey S. Lindquist, Maple Grove, MN (US); Ralph J. Barry, Hudson, MA (US); Kevin Silberg, Big Lake, MN (US); Ausberto Reyes Pineda, Somerville, MA (US); Chay Nil, Lynn, MA (US); Andrew J. Campbell, Reading, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 539 days.

(21) Appl. No.: 10/918,039

(22) Filed: Aug. 13, 2004

(65) Prior Publication Data
US 2006/0033241 A1     Feb. 16, 2006

(51) Int. Cl.
*B29C 49/64* (2006.01)
(52) U.S. Cl. ........................ 425/526; 425/392; 425/470; 249/79

(58) Field of Classification Search ................. 425/526, 425/522, 470, 392, 174.4; 249/79; 264/402, 264/521
See application file for complete search history.

(56) References Cited

U.S. PATENT DOCUMENTS

| | | | | |
|---|---|---|---|---|
| 5,017,325 | A * | 5/1991 | Jackowski et al. | 264/521 |
| 5,226,352 | A * | 7/1993 | Savage | 99/439 |
| 5,254,091 | A * | 10/1993 | Aliahmad et al. | 604/103.06 |
| 5,304,340 | A * | 4/1994 | Downey | 264/521 |
| 5,360,330 | A * | 11/1994 | Jensen et al. | 425/144 |
| 6,048,485 | A * | 4/2000 | Field et al. | 264/322 |
| 7,264,458 | B2 * | 9/2007 | Holman et al. | 425/174.4 |
| 2002/0103455 | A1 * | 8/2002 | Zhang et al. | 604/96.01 |

* cited by examiner

*Primary Examiner*—Robert B Davis
(74) *Attorney, Agent, or Firm*—Vidas, Arrett & Steinkraus

(57) ABSTRACT

A mold for a medical device balloon has a cavity adapted to receive a hollow parison expandable therein to form the balloon. The cavity has a cone region and a body region. The cone region is heated to a higher temperature, or the mold wall is formed to deliver applied heat more efficiently to the cone region, relative to the body region of the mold.

8 Claims, 4 Drawing Sheets

CATHETER BALLOON MOLDING DEVICE

FIELD OF THE INVENTION

This invention pertains to a mold apparatus for forming medical device parts such as balloons employed on catheters, endoscopes and the like.

BACKGROUND OF THE INVENTION

U.S. Pat. No. 4,490,421 Levy, and U.S. Pat. No. 5,264,260, Saab, describe PET balloons. U.S. Pat. No. 4,906,244, Pinchuk et al, and U.S. Pat. No. 5,328,468, Kaneko, describe polyamide balloons. U.S. Pat. No. 4,950,239, Gahara, and U.S. Pat. No. 5,500,180, Anderson et al describe balloons made from polyurethane block copolymers. U.S. Pat. No. 5,556,383, Wang et al, and U.S. Pat. No. 6,146,356, Wang et al, describe balloons made from polyether-block-amide copolymers and polyester-block-ether copolymers. U.S. Pat. No. 6,270,522, Simhambhatla, et al, describes balloons made from polyester-block-ether copolymers of high flexural modulus. U.S. Pat. No. 5,344,400, Kaneko, describes balloons made from polyarylene sulfide. U.S. Pat. No. 5,833,657, Reinhart et al, describes balloons having a layer of polyetheretherketone. All of these balloons are produced from extruded tubing of the polymeric material by a blow-forming radial expansion process.

In mass production of medical device balloons, some processes produce substantial rejection rates. Parison shaping techniques going beyond simple axial stretching and radial expansion of straight tubes tend to increase balloon rejection rates. Grinding or necking down ends of a parison may have such an effect. Nevertheless, shaped parisons are often needed, for instance to allow large diameter balloons to be fashioned with high burst strength and/or for mounting on small diameter catheters. A free-blowing step in a balloon forming process can also display such problems.

When molding balloons utilizing engineering polymer systems like polyamide derivatives, polyethylene terephthalate, and polybutylene terephthalate, the polymer material in the proximal and distal tapered cones typically results in a much higher average wall thickness versus that of the cylindrical balloon body portion. The above-mentioned balloon cone average wall thickness is typically much higher man what is actually required to provide adequate bunt strength. The problem of excessive wall thickness in the balloon cone areas has been addressed in a variety of ways. These have included removal of material from balloon cone walls via material ablation, chemically, mechanically or otherwise, from the balloon or the parison and modifications of a balloon preform by heating and drawing selective portions of the parison or balloon precursor. Examples of such techniques include U.S. Pat. No. 5,826,588, Forman; U.S. Pat. No. 6,458,313, Hudgins et al; U.S. Pat. No. 4,963,313, Noddin et al; U.S. Pat. No. 5,017,325, Jackowski et al; U.S. Pat. No. 5,334,146, Ozasa; U.S. Pat. No. 5,525,388, Wand et al; U.S. Pat. No. 5,714,110, Wang et al; U.S. Pat. No. 5,948,345, Patel; and U.S. Pat. No. 6,193,738, Tomaschko et al.

The ability to accurately and repeatably remove or reduce material in the balloon cone regions is important to successful, low profile peripheral vascular balloon deliverability through small introducer sheaths. While balloon cone thickness can be reduced in many ways, it is often difficult to obtain consistent results, especially when using prior art material removal techniques, whether they are applied to a preform or to the formed balloon. This is especially true with larger balloons that often must be used in peripheral vascular procedures.

U.S. Pat. No. 5,714,110, Wang et al., describes a method for forming a catheter balloon comprising the steps of placing tubing of a thermoplastic material in a mold and blowing the balloon by pressurizing and tensioning the tubing while gradually dipping the mold into a heated heat transfer media so as to sequentially blow the first waist, the body and the second waist portions of the balloon, the tubing being subjected to a relatively lower pressure while the body portion is blown than while the first and second waist portions are blown.

In U.S. Pat. No. 6,572,813, Zhang et al, an apparatus is described in which a mold form is heated by mechanically moving one or more external heaters along the outside of a balloon mold containing a tubular parison. The document states that the temperature of the parison, along the effective length of the mold should be kept within a specified minimum difference, for instance 100° C. and preferably within 20° C. That is, a relatively non-uniform heating apparatus is controlled to provide a more uniform heating. In this respect the system is understood to merely mimic heating behaviour of well known balloon molding systems, for instance those in which mold forms are dipped into a heated liquid bath and those in which a block heater surroundingly contacts the mold.

In copending U.S. patent application Ser. No. 10/753,043, filed Jan. 7, 2004, there is described an apparatus for forming a medical device balloon wherein the heating system applies heat differentially to predetermined parison initiation zone and remainder zone locations on the parison so that the initiation zone location is heated to a higher temperature than the remainder zone location for at least an initiation time period encompassing the initiation of blowing of the parison.

SUMMARY OF THE INVENTION

The present invention is directed to a novel mold design for preparing medical device balloons and to a balloon blowing process employing the mold design. The invention provides a catheter balloon molding system designed to facilitate balloon cone material wall thickness reduction and thereby provide more consistent, lower profile balloon components. The invention utilizes various methods to preferentially heat a balloon mold cone region, relative to the body region.

DETAILED DESCRIPTION OF PREFERRED EMBODIMENTS

Figure 1:
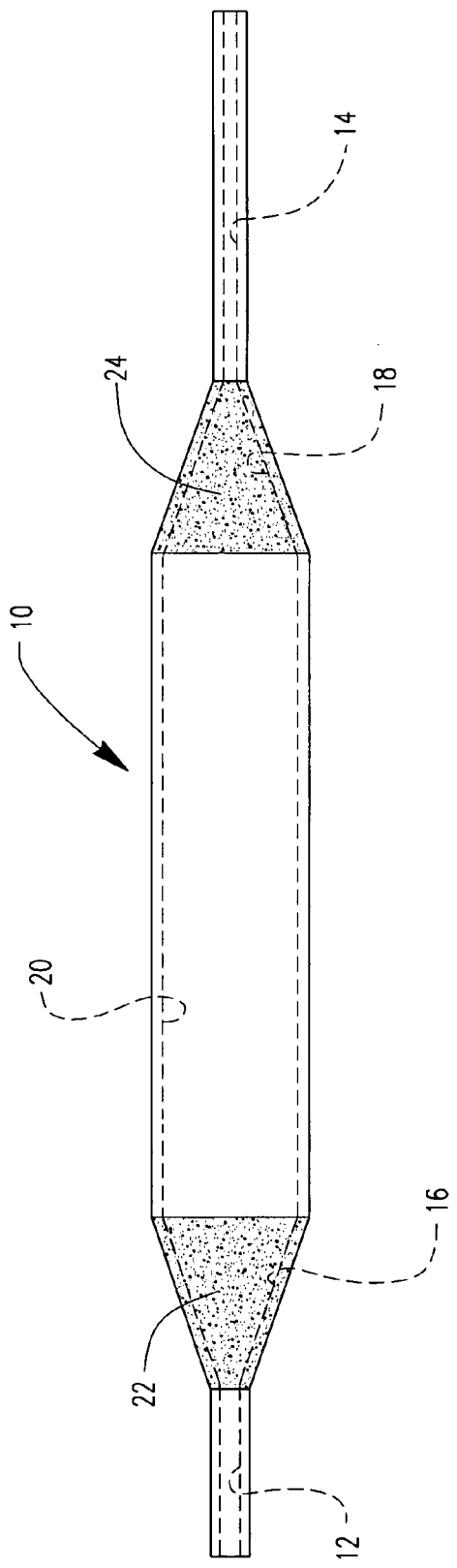
FIG. 1 is an exterior side view of a mold form according to one embodiment of the invention.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

In one aspect the invention is directed to an apparatus for molding a medical device balloon, the apparatus comprising
   a mold form having an interior cavity the interior cavity having at least one cone region and a body region, respectively shaped to define corresponding portions of said balloon, and
   a heating system for heating the mold form,
   wherein
   the heating system is configured to heat said cone region of the interior cavity of the mold to a higher temperature than the body region during balloon molding.

In another aspect the invention is a mold form for a medical balloon, the mold form including at least one cone region and a body region, the mold wall adapted to receive energy applied to the exterior surface thereof and to transmit it to the inner surface at a greater efficiency over the cone region than over the body region.

In a yet another aspect the invention is a mold form for a medical balloon, the mold form including at least one cone region and a body region wherein the mold form has a hollow wall portion over the cone region, and entry and exit ports communicating with the hollow wall portion.

In another aspect the invention is a process for molding a medical device balloon comprising:
   placing a parison in a mold form having an interior cavity, the interior cavity having at least one cone region and a body region, the cone and body regions respectively shaped to define corresponding portions of said balloon;
   heating the mold and
   pressurizing the parison to radially expand the parison to contact and conform to the inner cavity,
   wherein
      the heated mold provides a higher temperature at said cone region than at said body region.

Still further aspects of the invention are described or are readily apparent from the following description, the accompanying drawings and the claims.

In various embodiments the inventive apparatus may utilize one or more of the following techniques to induce a thermal transfer differentiation or heating differentiation specific to a cone region of the mold:
   light absorbing coatings on selective portions of the external surface of the balloon mold in processes where light energy is used to heat the mold;
   differential thickness of the balloon mold wall in the cone and body regions;
   mold walls having portions of different materials which have different thermal conductivity properties;
   separate heating systems for cone and body regions; and
   selective shading of a balloon wall portion from a heat source.

The increased temperature of the cone region may be from about 2° C. to about 100° C. higher, for instance, from about 5° C. to about 30° C. higher, or from about 7° C. to about 15° C. than the blowing temperature, i.e. the temperature to which the body region is heated. The body region may be heated to a temperature at which the particular material will form a balloon by pressurization in conventional manner. The blowing temperature may be at least 10° C., more preferably about 20° C. or more, and in some cases may be 40° C. or more, above the glass transition temperature of the polymeric material forming the parison. In the case of a block copolymer these temperatures are typically taken relative to the highest glass transition temperature of the material. Typically the temperature to which the body region is heated is from about 80° C. to about 150° C. for most thermoplastic materials used to form medical balloons for catheters and the like.

FIGS. 1-4 illustrate different embodiments of mold forms of the present invention. The exterior shape of the mold forms of these particular embodiments are generally quite similar to the shape of the interior mold cavity. However it should be noted that the balloon form is defined by the inner surfaces of the mold form cavities of these devices, not the exterior configuration. Consequently, for at least some embodiments of the invention, it is not necessary that the outer and inner surfaces correspond to each other in any substantial way.

In FIG. 1, a mold form 10 is shown. Mold form 10 has an interior cavity, shown in phantom. The interior cavity includes waist regions 12, 14, cone regions 16, 18 and body region 20. The exterior surfaces 22, 24 of mold 10, overlying the interior cone regions 16, 18, are coated with a material that absorbs light energy more efficiently than the remaining exterior surfaces of the device. This may be, for instance a black coating, especially if the mold is heated by an infrared or visible light source.

The mold is constructed of a heat transmissible material, typically metals such as aluminum, titanium, stainless steel, cladded copper, or the like. The mold is adapted to be heated by light energy, for instance by directing the output of one or more infrared lamps (not shown) at the exterior of the mold. Because of the light absorbing coating on exterior cone regions 22, 24, the interior cone regions 16, 18 are heated to a higher temperature than the interior waist and body regions 12, 14, and 20. Other factors remaining constant, a balloon formed in mold 10, with application of external heat energy will have thinner cone walls than if an uncoated, mold were used.

The light energy applied may comprise infrared wavelengths or and/or any wavelengths outside the infrared which may be absorbed to produce heating of the mold. In at least some instances light in the visible or UV spectrum will give effective heating of the mold. The light energy may be essentially monochromatic, as is produced by a laser light source. Broader spectrum sources such as halogen lamps, xenon flash lamps, mercury lamps, tungsten filament lamps, and the like, may also be used. The light beam may be pulsed and the mold or light source may be moved as needed to achieve the desired level of heating in an initiation zone configured as desired. Preferably optics are employed which apply the light energy concurrently around the circumference of the parison initiation zone 20.

In a variation of the embodiment of FIG. 1, the waist regions may also be provided with the light absorptive coating.

In a another embodiment of the invention, similar to that of FIG. 1, the exterior surface of the mold form overlying the body region may be provided with a heat reflective coating, with or without the use of a heat absorbing coating in the cone region. Selective anodization and/or polishing of mold surfaces can be used to impart different absorption characteristics to the mold surface. When light energy applied to the external surface of the mold form the mold cavity surfaces under the reflective coating will be cooler than the mold cavity surfaces under the uncoated or light absorbing coated portions.

Figure 2:
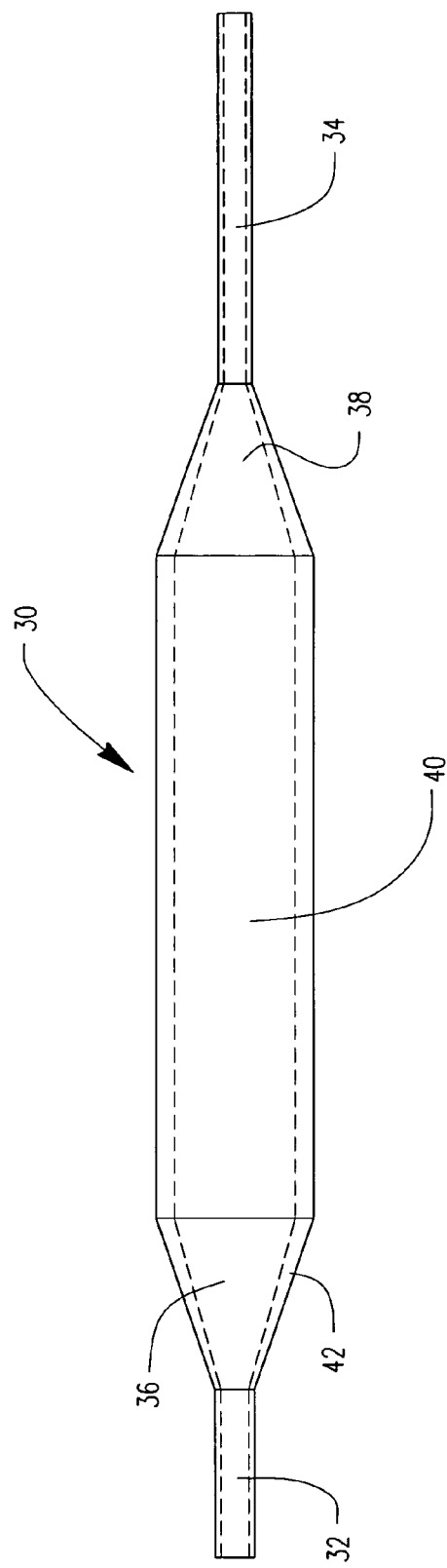
FIG. 2 is an exterior side view of a mold form according to another embodiment of the invention.

FIG. 2 depicts another embodiment of the invention. The exterior of a mold form 30 is shown, with respective waist regions 32, 34, cone regions 36, 38 and body region 40 and body regions. The inner cavity wall is depicted in phantom. The wall thickness of the mold in the body region 40 is uniform, but thins in the cone regions 36, 38, and the waist regions 32, 34, so that heat energy applied externally, for instance, by immersion in hot liquid or by application of IR energy, is more efficiently transferred to the interior cavity wall in the cone and waist regions. Other factors remaining constant, the cone and waist regions of a balloon produced in this mold, with application of external heat energy, will be thinner than those of a balloon produced in a mold which has a wall thickness in the waist, cone and body regions that is the same as the thickness of the body region of the FIG. 2 mold.

In variations of the embodiment of FIG. 2, the cone regions may be provided with a constant thickness, thinner than the body region and/or the waist region may have a wall thickness substantially the same as the body region.

Figure 3:
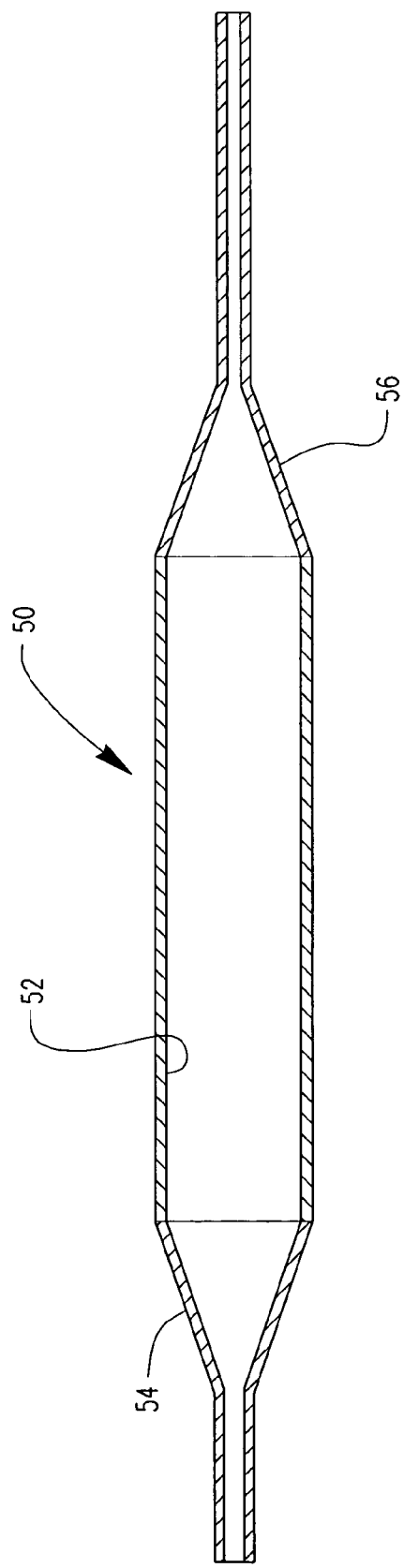
FIG. 3 is an side sectional view of a mold form according to a third embodiment of the invention.

FIG. 3 depicts yet another embodiment of the invention. A segmented mold form 50 is shown in cross-section. The body-forming segment 52 is formed of a first material. The cone-waist forming segments 54, 56 are formed of a second, different material. The second material has higher heat conductivity than the first material. When heat energy is applied to the exterior surface of the mold, the energy is more efficiently transferred to the interior wall of the cone-waist segments than the body segment. Other factors remaining constant, the cone and waist regions of a balloon produced in this mold, with application of external heat energy, will be thinner than those produced in a mold which has the same wall material in the cone-waist section as in the body section.

In variations of the embodiment of FIG. 3, the wall material of the cone regions and the waist regions may be different, for instance the waist region material may be substantially the same as the body region material.

Figure 4:
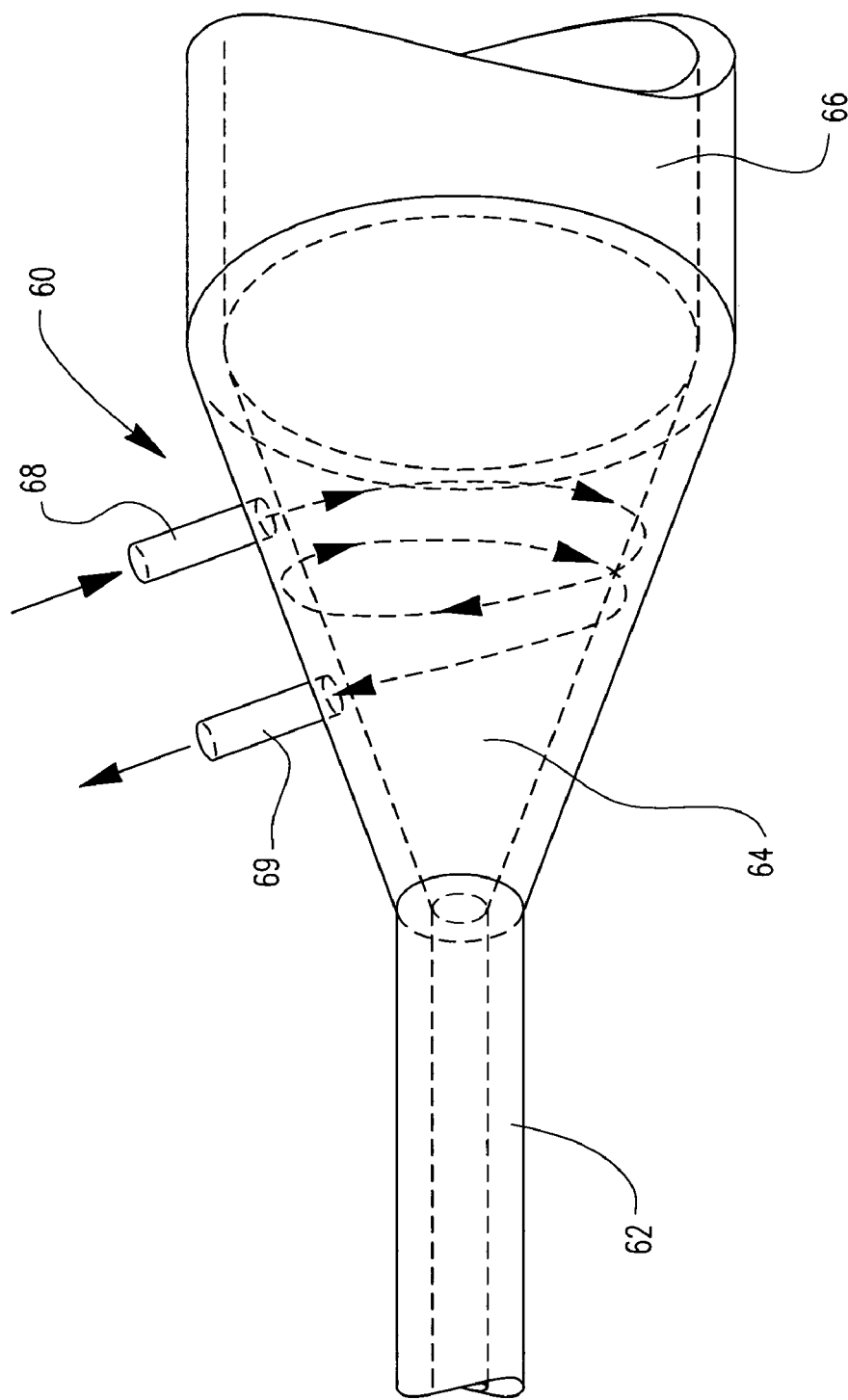
FIG. 4 is a schematic fragmentary side exterior view of a fourth embodiment of the invention.

FIG. 4 depicts a still further embodiment of the invention. A portion of a mold form 60 is shown, including a waist portion 62, a cone portion 64 and a body portion 66. The waist and body portions are formed of substantially solid material. In the cone portion 64, however, the mold wall is hollow, with fluid access to the interior space thereof being provided by the entrance and exit ports 68, 69, respectively. The mold may be heated for instance by immersion in a hot fluid bath. The desired temperature differential is provided to the cone region by circulating fluid through the hollow wall of cone portion 62 at a higher temperature than that of the bath. The exit port 69 may be connected to recirculate the heated fluid or to direct the exiting fluid to waist.

In a variation of the embodiment of FIG. 4, the hollow wall portion may be extended over the waist. In another variation primary heating may be provided by a light source. In yet another alternative the body portion 66 may be provided with a separate hollow wall, an access port communicating with a fluid source which provides heated fluid at a lower temperature than the fluid provided to the cone, and an exit port.

In yet another embodiment of the invention, partial shielding may be disposed between a heat source and a mold exterior. The partial shielding selectively blocks a portion of the heat source output directed at the body region, but not that directed at a cone region. Suitable shielding may be a heat reflective ceramic material, optionally provided with holes therethrough to allow some heat passage therethrough.

It should be noted that the invention contemplates at least one cone region can be differentially heated relative to a body portion of the mold. Most balloon forms have two cone regions. In some embodiments both such cone regions are heated with substantially the same differential. However, in some cases it may be advantageous to employ different differentials for each cone region or to provide a differential at only one of the cone regions with the second being heated the same as the body portion.

Moreover, more complex shapes, such as stepped balloons, may be employed which have more than two cone regions. See for instance U.S. Pat. No. 6,290,485. In molding such balloons any step may be taken as the body region for reference and any positive integer number of the available cone regions may be provided with the heating differential therebetween.

The mold form may be configured to open or disassemble, to facilitate removal of the formed balloon. For a mold design as depicted in FIGS. 1-4 a segmented configuration, for instance as depicted in FIG. 4 of U.S. Pat. No. 6,328,710, may be employed. Clam shell opening mechanisms, or other mold designs which mate two longitudinal sections, may also be employed in designing mold forms of the invention.

The mold form may be provided with suitable sensors, such as thermocouples, to monitor temperature of various regions. Such sensors may feed back to an automated heating control system.

In systems employing a heated fluid bath as primary heating, thermal transfer therefrom can be further facilitated by agitation of the fluid and/or vibration of the bath apparatus, for instance by ultrasonic vibration.

Mold forms of the invention may be made of any suitable material, preferably one which provides for a highly polished or glassy cavity surface. Metal, such as titanium or stainless steel, are exemplary materials. Glass and ceramic materials may also be employed. Composite and laminate materials are also suitable. Preferred are materials which have high heat conductivity, especially metals such as stainless steel, titanium, aluminum and the like.

Any balloon material suited to molding may be employed in the inventive method. Balloon materials which may be advantageously employed in the invention are well known. Any material which can be molded from a parison may be feasibly employed in the invention. Such materials include polyesters such as PET, PEN and PBT, polyurethane block copolymers such as ISOPLAST 301, PELLETHANE 2363-75D, and other materials described in U.S. Pat. No. 4,950,239 or U.S. Pat. No. 5,500,180; polyamide block copolymers such as PEBAX 6333, PEBAX 7033 and PEBAX 7233, and other materials described in U.S. Pat. No. 5,556,383; polyamides such as nylon 12, nylon 11, nylon 10, and other materials described in U.S. Pat. No. 4,906,244; polymer blend materials such as single or multiphase blends of liquid crystal polymers in another polymer, such as described in U.S. Pat. No. 6,242,063, U.S. Pat. No. 6,284,333 or U.S. Pat. No. 6,596,219; and polyester elastomer balloons such as ARNITEL EM 740, HYTREL 8238, and other materials described in U.S. Pat. No. 5,556,383 or U.S. Pat. No. 6,270,522.

The balloon parison may be a straight tube, as extruded, or after extrusion and axial stretching. The tubular parison is not necessarily homogenous along its length. The parison may be multilayered, using the same or different materials in the various layers. It may have a varying thickness, for instance resulting from parison processing such as the necking steps described in U.S. Pat. No. 4,963,313, Noddin, et al; U.S. Pat. No. 5,556,383, Wang, et al; or U.S. Pat. No. 5,087,394, Keith, or grinding steps such as described in U.S. Pat. No. 6,193,738, Tomaschko et al. The balloon mold may have a multiple-stepped diameter such as described in U.S. Pat. No. 6,290,485, Wang. The parison may be formed of longitudinal segments of different materials such as described in U.S. Pat. No. 6,024,752, Horn et al.

A variety of blow forming techniques have been utilized. Examples of these techniques may be found in the patent documents already mentioned or in U.S. Pat. No. 5,306,246 Sahatjian; U.S. Pat. No. 4,935,190, Tennerstedt; U.S. Pat. No. 5,714,110, Wang et al; U.S. Pat. No. 5,304,340, Downey.

A typical method for blowing a balloon comprises extruding a polymeric tubular parison having a first outer diameter. The tubular parison is then radially expanded to a second outer diameter, optionally with a concurrent or intermediate axial stretching step. Radial expansion is accomplished by heating at least a portion of the tubular parison to a first elevated temperature while subjecting the interior of the tubular parison to an expansion pressure. In some embodiments axial stress is provided to further stretch the parison during radial expansion, or to at least counteract a tendency of prestretched parisons to longitudinally retract during radial expansion.

Following blow-forming the balloons may be simply cooled; "heat set" at a still higher pressure and/or temperature than the blow-forming temperature and/or pressure; or "heat shrunk" at an above-ambient pressure and temperature, at least one of which is lower than the blow-forming temperature and pressure. See U.S. Pat. No. 5,403,340, Wang et al; EP 540858, Advanced Cardiovascular Systems, Inc.; and WO 98/03218, Scimed Life Systems.

The invention may be used in preparation of high strength medical balloons of any type. Particular advantages are in peripheral vascular applications where large differential between catheter diameter and balloon diameter is desirable. Suitably the balloons are formed by expansion of tubing at a hoop ratio (mold diameter/tubing ID) of between 3 and 8, preferably between 4 and 7, although other ratios may be suitable for some applications.

Combinations of the techniques and systems described herein may also be employed.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to." Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. An apparatus for molding a medical device balloon, the apparatus comprising
   a mold form having an interior cavity the interior cavity having at least one cone region and a body region, respectively shaped to define corresponding portions of said balloon, and
   a heating system for heating the mold form,
   wherein
   the heating system is configured to heat said cone region of the interior cavity of the mold to a higher temperature than the body region during balloon molding, the mold form has an exterior surface to which energy is applied to heat the mold cavity, and a mold wall is defined between the interior cavity of the mold form and the exterior surface thereof and the mold wall is thinner in the cone region than in the body region.

2. An apparatus as in claim 1 wherein the mold form inner cavity has at least one waist region, and the mold wall is thinner in the waist region than in the body region.

3. An apparatus for molding a medical device balloon, the apparatus comprising
   a mold form having an interior cavity the interior cavity having at least one cone region and a body region, respectively shaped to define corresponding portions of said balloon, and
   a heating system for heating the mold form,
   wherein
   the heating system is configured to heat said cone region of the interior cavity of the mold to a higher temperature than the body region during balloon molding, the heating system comprises a first heating apparatus for heating said cone region and a second heating apparatus for heating at least the body region, and the mold form has a hollow wall portion over the cone region, and ports communicating therewith whereby heating fluid may be selectively provided to the hollow wall portion.

4. An apparatus for molding a medical device balloon, the apparatus comprising
   a mold form having an interior cavity the interior cavity having at least one cone region and a body region, respectively shaped to define corresponding portions of said balloon, and
   a heating system for heating the mold form,
   wherein
   the heating system is configured to heat said cone region of the interior cavity of the mold to a higher temperature than the body region during balloon molding, the heating system comprises a first heating apparatus for heating said cone region and a second heating apparatus for heating at least the body region, the mold form has a solid wall portion over the body portion and the second heating apparatus is configured to apply heat at least to said solid wall portion, and the second heating apparatus comprises an heated fluid bath into which at least a portion of the mold form may be immersed during balloon blowing.

5. An apparatus as in claim 4 wherein the mold form has a hollow wall portion over the cone region, an entry port and an exit port communicating with the hollow wall portion, and the first heating apparatus comprises a heated fluid source independent of said heated fluid bath said heated fluid source communicating with at least said entry port.

6. A mold form for a medical balloon, the mold form having mold wall defining an interior cavity the interior cavity having at least one cone region and a body region, respectively shaped to define corresponding portions of said balloon, the mold wall further having an exterior surface, the mold wall adapted to receive energy applied to the exterior surface thereof and to transmit it to the inner surface at a greater efficiency over the cone region than over the body region, wherein the wall thickness of the mold wall in the body region is greater than in the cone region.

7. A mold form for a medical balloon, the mold form having mold wall defining an interior cavity the interior cavity having at least one cone region and a body region, respectively shaped to define corresponding portions of said balloon, the mold wall further having an exterior surface, the mold wall adapted to receive energy applied to the exterior surface thereof and to transmit it to the inner surface at a greater efficiency over the cone region than over the body region, wherein the interior cavity further comprises at least one waist region shaped to define a waist portion of the balloon, the mold wall in the waist region being thinner than in the body region, and the mold wall in the cone region tapering in thickness between the body and waist regions.

8. A mold form for a medical balloon, the mold form having a mold wall defining an interior cavity, the interior cavity having at least one cone region and a body region, the cone and body regions respectively shaped to define corresponding portions of said balloon, wherein the mold form has a hollow wall portion over the cone region, an entry port and an exit port communicating with the hollow wall portion, wherein the mold wall is substantially solid over the body region.

* * * * *